United States Patent
Maeda (10) Patent No.: US 12,155,919 B2
(45) Date of Patent: Nov. 26, 2024

(54) MANUFACTURING METHOD OF IMAGE PICKUP APPARATUS FOR ENDOSCOPE, IMAGE PICKUP APPARATUS FOR ENDOSCOPE, AND ENDOSCOPE

(71) Applicant: OLYMPUS CORPORATION, Tokyo (JP)

(72) Inventor: Kazuya Maeda, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 600 days.

(21) Appl. No.: 17/464,169

(22) Filed: Sep. 1, 2021

(65) Prior Publication Data

US 2021/0396975 A1 Dec. 23, 2021

Related U.S. Application Data

(63) Continuation of application No. PCT/JP2019/019095, filed on May 14, 2019.

(51) Int. Cl.
*H04N 23/55* (2023.01)
*B29D 11/00* (2006.01)
(Continued)

(52) U.S. Cl.
CPC ....... *H04N 23/55* (2023.01); *B29D 11/00307* (2013.01); *B29D 11/0074* (2013.01);
(Continued)

(58) Field of Classification Search
None
See application file for complete search history.

(56) References Cited

U.S. PATENT DOCUMENTS 8,711,483 B2 4/2014 Matsuno et al.
9,044,139 B2 * 6/2015 Takahashi ............ A61B 1/0055
(Continued)

FOREIGN PATENT DOCUMENTS

CN 103392141 A * 11/2013 ....... B29D 11/00307
EP 2 682 797 A1 1/2014
(Continued)

OTHER PUBLICATIONS

Miyagawa JP2009047949A 2009 English Translation (Year: 2009).*
(Continued)

*Primary Examiner* — Jacob T Minskey
*Assistant Examiner* — Adrien J Bernard
(74) *Attorney, Agent, or Firm* — Scully, Scott, Murphy & Presser, P.C.

(57) ABSTRACT

A manufacturing method of an image pickup apparatus for endoscope includes: fabricating a first optical wafer and a second optical wafer including spacers; disposing walls made of a first resin, being greater in height than the spacers, and enclosing optical paths without any gap; clamping the first optical wafer and the second optical wafer with the walls being interposed between the first optical wafer and the second optical wafer; charging a second resin around the walls; performing curing treatment on the second resin to cause the second resin to shrink, and fix the first optical wafer and the second optical wafer in a state where an interval between the first optical wafer and the second optical wafer is defined by the spacers; and cutting a bonded wafer.

20 Claims, 8 Drawing Sheets

(51) Int. Cl.
  *G02B 7/02* (2021.01)
  *G02B 13/00* (2006.01)
  *G02B 23/24* (2006.01)
  *A61B 1/00* (2006.01)
  *A61B 1/05* (2006.01)
  *B29K 69/00* (2006.01)
  *H04N 23/50* (2023.01)

(52) U.S. Cl.
  CPC ......... *G02B 7/021* (2013.01); *G02B 13/0065* (2013.01); *G02B 23/243* (2013.01); *A61B 1/0011* (2013.01); *A61B 1/051* (2013.01); *B29K 2069/00* (2013.01); *B29K 2995/0026* (2013.01); *H04N 23/555* (2023.01)

(56) References Cited

U.S. PATENT DOCUMENTS

| | | | | |
|---|---|---|---|---|
| 10,386,616 | B2* | 8/2019 | Mouws | B29D 11/00307 |
| 11,130,299 | B2* | 9/2021 | Tazawa | B29D 11/00375 |
| 2019/0090720 | A1 | 3/2019 | Maeda | |

FOREIGN PATENT DOCUMENTS

| | | |
|---|---|---|
| JP | H08-201837 A | 8/1996 |
| JP | 2001-160229 A | 6/2001 |
| JP | 2004-133073 A | 4/2004 |
| JP | 2006-010959 A | 1/2006 |
| JP | 2006-025091 A | 1/2006 |
| JP | 2009-047949 A | 3/2009 |
| JP | 2010-066730 A | 3/2010 |
| JP | 4764942 B2 | 9/2011 |
| JP | 2013-076769 A | 4/2013 |
| WO | 2012/117986 A1 | 9/2012 |
| WO | 2017/212520 A1 | 12/2017 |

OTHER PUBLICATIONS

Matsuno CN103392141A 2013 English Translation (Year: 2013).*
International Search Report dated Aug. 6, 2019 received in PCT/JP2019/019095.

* cited by examiner

MANUFACTURING METHOD OF IMAGE PICKUP APPARATUS FOR ENDOSCOPE, IMAGE PICKUP APPARATUS FOR ENDOSCOPE, AND ENDOSCOPE

CROSS REFERENCE TO RELATED APPLICATION

This application is a continuation application of PCT/JP2019/019095 filed on May 14, 2019, the entire contents of which are incorporated herein by this reference.

BACKGROUND OF THE INVENTION

1. Field of the Invention

The present invention relates to a manufacturing method of an image pickup apparatus for endoscope formed by stacking a plurality of optical devices, an image pickup apparatus for endoscope formed by stacking a plurality of optical devices, and an endoscope including an image pickup apparatus for endoscope formed by stacking a plurality of optical devices.

2. Description of the Related Art

In an image pickup apparatus for endoscope to be disposed in a distal end portion of an endoscope, size reduction, in particular, reduction in a diameter size is important to minimize invasiveness.

International Publication No. 2017-212520 discloses, as a method of efficiently manufacturing an image pickup apparatus, an image pickup apparatus having an optical unit composed of a wafer-level stacked body. The wafer-level optical unit is fabricated by cutting and dividing a bonded wafer formed by gluing a plurality of optical wafers each including a plurality of optical devices. For gluing the optical wafers, a solid first gluing material for adjusting an optical path length and a liquid second gluing material are used.

SUMMARY OF THE INVENTION

A manufacturing method of an image pickup apparatus for endoscope according to an embodiment of the present invention includes: fabricating a first optical wafer including a first principal surface and a second principal surface on an opposite side of the first principal surface, and including a plurality of first optical devices, and a second optical wafer including a third principal surface and a fourth principal surface on an opposite side of the third principal surface, and including a plurality of second optical devices respectively including spacers on the third principal surface; disposing a plurality of walls on the second principal surface or the third principal surface, the plurality of walls being made of a first resin, being greater in height than the spacers, and enclosing respective optical paths without any gap; sealing the optical paths by clamping the second principal surface and the third principal surface with the walls being interposed between the second principal surface and the third principal surface; charging a second resin between the second principal surface and the third principal surface around the walls, the second resin being uncured and liquid; performing curing treatment on the second resin to cause the second resin to shrink, and fix the second principal surface and the third principal surface in a state where an interval between the second principal surface and the third principal surface is defined by the spacers; and cutting a bonded wafer in which the first optical wafer and the second optical wafer are fixed by the second resin.

An image pickup apparatus for endoscope according to an embodiment includes an optical unit, and an image pickup unit configured to receive an object image focused by the optical unit. The optical unit includes a first optical member including a first principal surface and a second principal surface on an opposite side of the first principal surface, a second optical member including a third principal surface and a fourth principal surface on an opposite side of the third principal surface, the third principal surface being opposed to the second principal surface, the second optical member including a spacer on the third principal surface around an optical path, the spacer defining an interval between the second principal surface and the third principal surface, a first resin constituting a wall that seals the optical path between the second principal surface and the third principal surface, is equal in height to the spacer, and encloses the optical path without any gap, and a second resin charged around the wall and being equal in height to the spacer. The first resin is smaller in hardness than the second resin.

An endoscope according to an embodiment includes an image pickup apparatus for endoscope. The image pickup apparatus for endoscope includes an optical unit, and an image pickup unit configured to receive an object image focused by the optical unit. The optical unit includes a first optical member including a first principal surface and a second principal surface on an opposite side of the first principal surface, a second optical member including a third principal surface and a fourth principal surface on an opposite side of the third principal surface, the third principal surface being opposed to the second principal surface, the second optical member including a spacer on the third principal surface around an optical path, the spacer defining an interval between the second principal surface and the third principal surface, a first resin constituting a wall that seals the optical path between the second principal surface and the third principal surface, is equal in height to the spacer, and encloses the optical path without any gap, and a second resin charged around the wall and being equal in height to the spacer. The first resin is smaller in hardness than the second resin.

DETAILED DESCRIPTION OF THE PREFERRED EMBODIMENT

<Endoscope>

Figure 1:
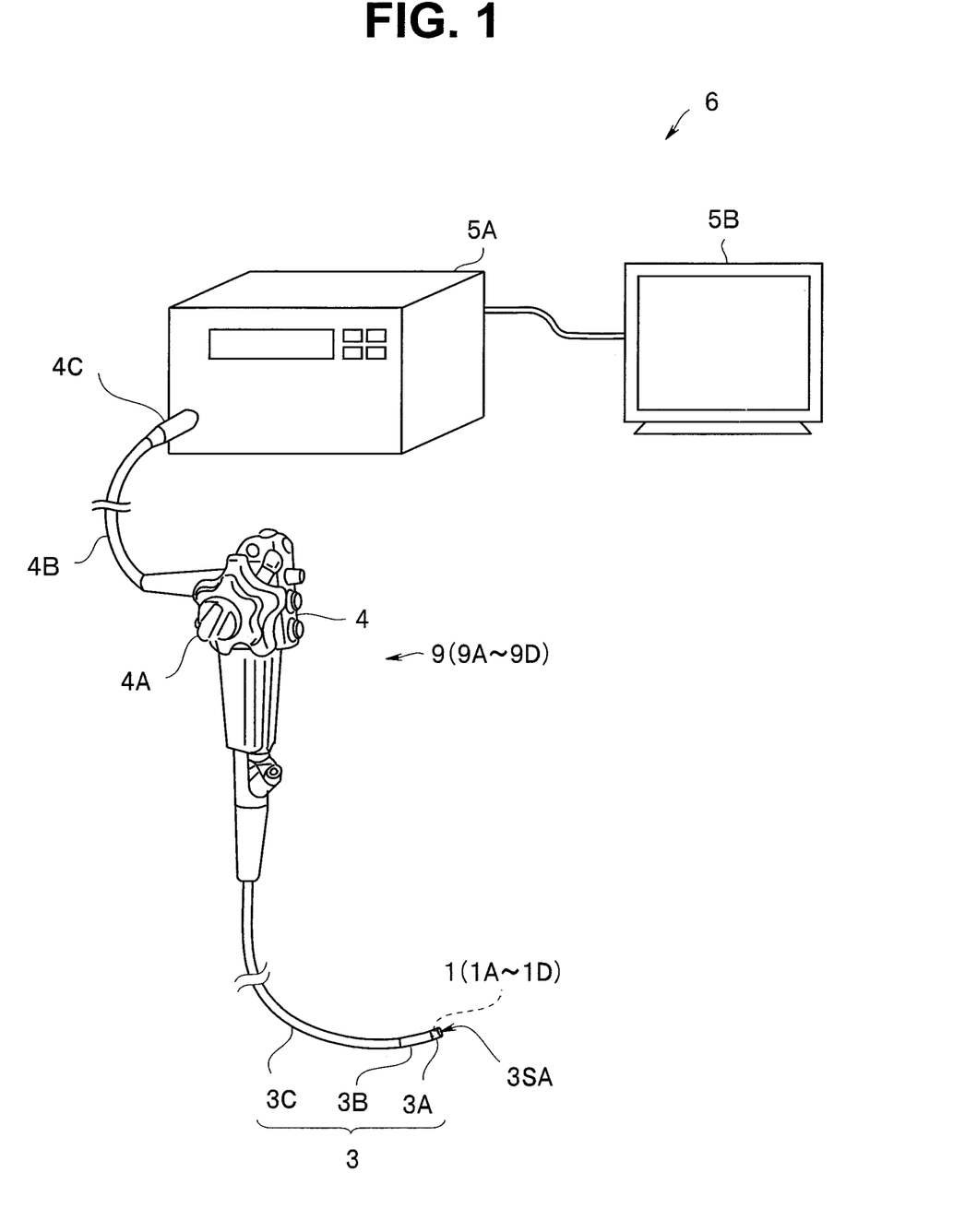
FIG. 1 is a configuration diagram of an endoscope system including an endoscope according to an embodiment.
Figure 2:
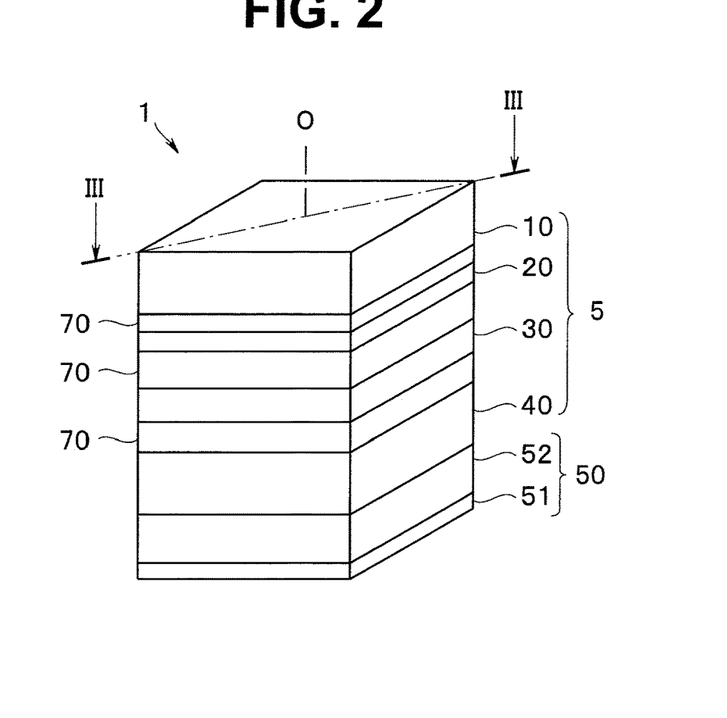
FIG. 2 is a perspective view of an image pickup apparatus according to an embodiment.

An endoscope 9 according to an embodiment shown in FIG. 1 constitutes an endoscope system 6 in conjunction with a processor 5A and a monitor 5B.

The endoscope 9 includes an insertion section 3, a grasping section 4 disposed on a proximal end portion of the insertion section 3, a universal cord 4B extended from the grasping section 4, and a connector 4C disposed on a proximal end portion of the universal cord 4B. The insertion section 3 includes a distal end portion 3A, a bending portion 3B extended from the distal end portion 3A and configured to be bendable to change a direction of the distal end portion 3A, and a flexible portion 3C extended from the bending portion 3B. An angle knob 4A configured to rotate is disposed on the grasping section 4. The angle knob 4A is an operation portion configured to be operated by an operator to operate the bending portion 3B.

The universal cord 4B is connected to the processor 5A through the connector 4C. The processor 5A is configured to control the endoscope system 6 as a whole, and perform signal processing on an image pickup signal to output the processed signal as an image signal. The monitor 5B is configured to display the image signal outputted from the processor 5A as an endoscopic image. Note that the endoscope 9 is a flexible endoscope, but may be a rigid endoscope. The endoscope 9 may be for a medical purpose or an industrial purpose.

As will be described later, an image pickup apparatus for endoscope 1 (hereinafter also referred to as an "image pickup apparatus") disposed on the distal end portion 3A has a favorable optical property and high reliability. Therefore, the endoscope 9 has a favorable optical property and high reliability.

<Image Pickup Apparatus>

As shown in FIG. 2 to FIG. 5, the image pickup apparatus for endoscope 1 according to an embodiment has an optical unit 5 and an image pickup unit 50. The optical unit 5 is a stacked body formed by stacking a plurality of optical devices 10 to 40.

Note that in the description below, the drawings based on respective embodiments are schematic, and a relationship between thickness and width of each portion, a ratio between thicknesses, a relative angle, and the like of respective portions are different from actual ones. Among the drawings, portions that are different in mutual dimensional relationship and ratio may be included. Illustration of some components may be omitted.

As will be described later, the optical unit 5 is a wafer-level stacked body fabricated by cutting a bonded wafer. Therefore, the optical unit 5 has a rectangular parallelepiped shape, and the optical devices 10 to 40 all have a rectangular sectional shape in a direction orthogonal to an optical axis, and have the same outer dimensions. The optical devices 10 to 40 are stacked such that the optical devices 10 to 40 have the same optical axis O.

Figure 5:
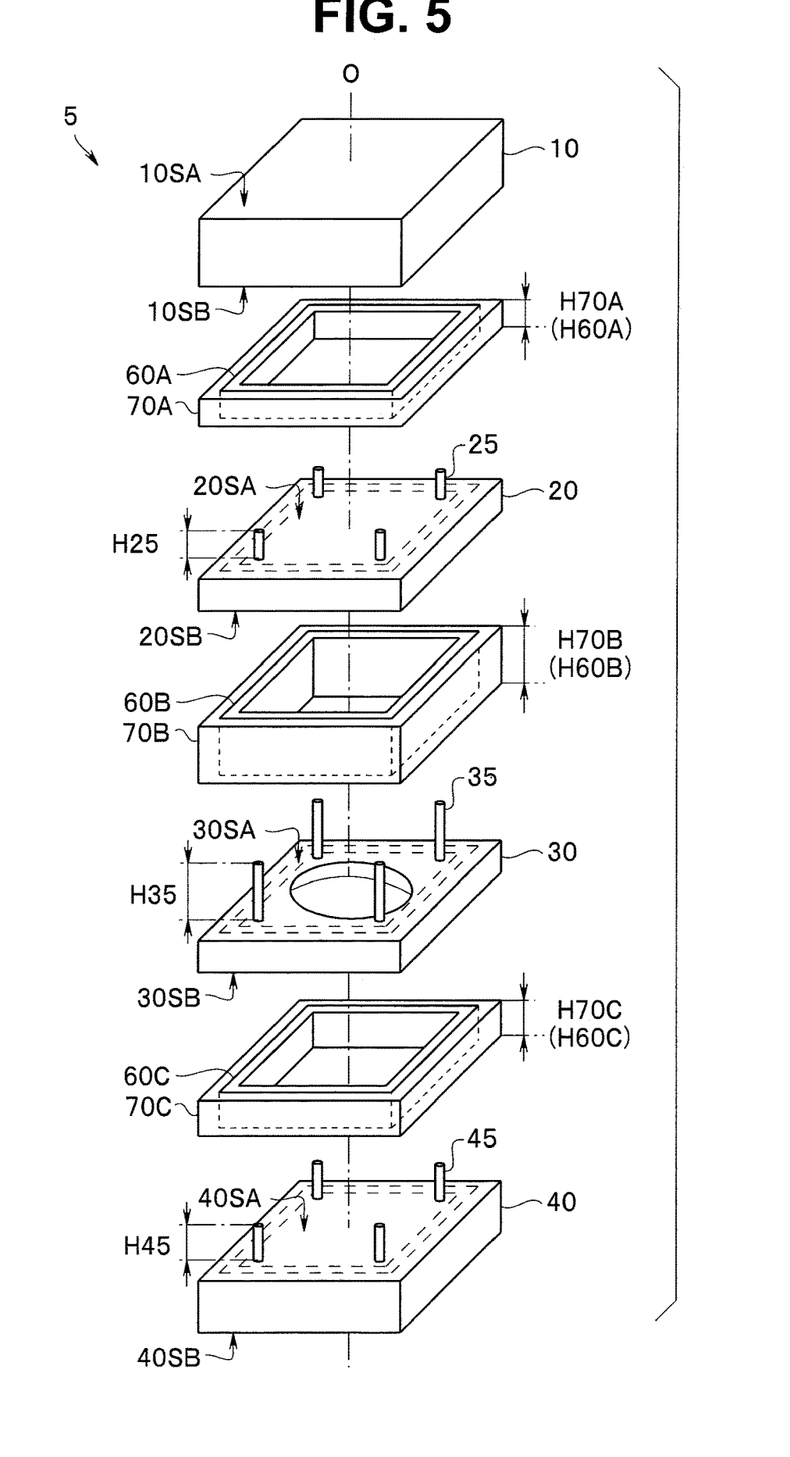
FIG. 5 is an exploded view of the image pickup apparatus according to an embodiment.

An optical device 10 which is a first optical member has a first principal surface 10SA and a second principal surface 10SB on an opposite side of the first principal surface 10SA. The optical device 10 is a plano-concave lens in which the first principal surface 10SA is a flat surface, and the second principal surface 10SB is a concave lens.

An optical device 20 which is a second optical member has a third principal surface 20SA and a fourth principal surface 20SB on an opposite side of the third principal surface 20SA. The optical device 20 is a plano-convex lens in which the third principal surface 20SA is a flat surface, and the fourth principal surface is a convex lens.

An optical device 30 which is a third optical member has a fifth principal surface 30SA and a sixth principal surface 30SB on an opposite side of the fifth principal surface 30SA. The optical device 30 is a convex-plano lens.

An optical device 40 which is a fourth optical member has a seventh principal surface 40SA and an eighth principal surface 40SB on an opposite side of the seventh principal surface 40SA. The optical device 40 is an infrared cut filter configured to remove infrared light (for example, light having a wavelength of more than or equal to 700 nm). The filter may be a glass filter in which a bandpass filter is disposed on a surface. The bandpass filter is configured to only transmit light having a predetermined wavelength, and cut light having an unnecessary wavelength.

The optical device 20 has spacers 25 which are columns having a height H25 on the third principal surface 20SA. The optical device 30 has spacers 35 which are columns having a height H35 on the fifth principal surface 30SA. The optical device 40 has spacers 45 which are columns having a height H45 on the seventh principal surface 40SA.

Figure 4:
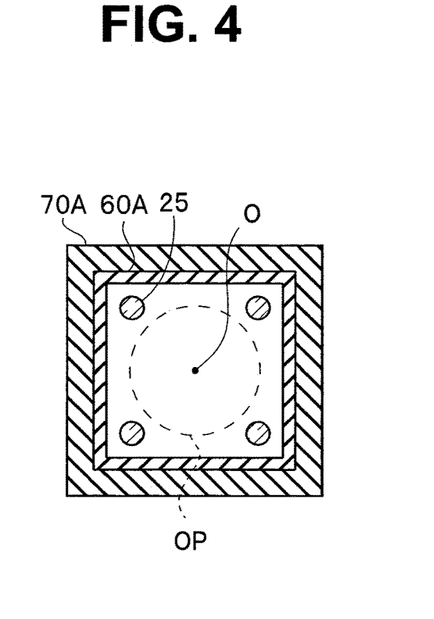
FIG. 4 is a sectional view taken along a line VI-VI in FIG. 3.

As shown in FIG. 4, a frame-like first resin 60A that encloses an optical path OP without any gap and a second resin 70A charged around the first resin 60A are disposed around the optical path OP between the second principal surface 10SB and the third principal surface 20SA opposite to the second principal surface 10SB.

Figure 3:
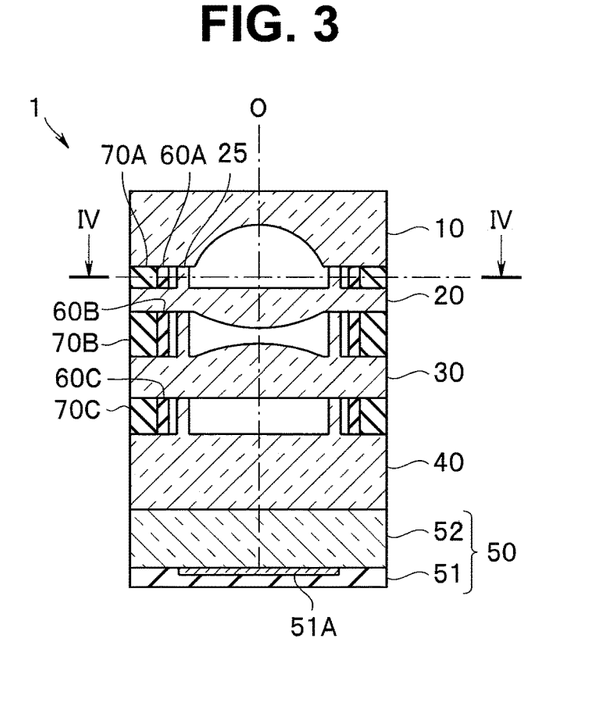
FIG. 3 is a sectional view taken along a line III-III in FIG. 2.

Similarly, a frame-like first resin 60B that encloses the optical path OP without any gap and a second resin 70B charged around the first resin 60B are disposed between the fourth principal surface 20SB and the fifth principal surface 30SA. A frame-like first resin 60C that encloses the optical path OP without any gap and a second resin 70C charged around the first resin 60C are disposed between the sixth principal surface 30SB and the seventh principal surface 40SA.

A distance between the second principal surface 10SB and the third principal surface 20SA is defined by the height H25 of the spacers 25. Therefore, a height H60A of the first resin 60A and a height H70A of the second resin 70A are equal to the height H25 of the spacers 25.

Similarly, a height H60B of the first resin 60B and a height H70B of the second resin 70B are equal to the height H35 of the spacers 35. A height H60C of the first resin 60C and a height H70C of the second resin 70C are equal to the height H45 of the spacers 45.

Note that the first resins 60A to 60C are resins of the same type, and the second resins 70A to 70C are resins of the same type. Hereinafter, when referring to each of a plurality of similar components, an alphabet letter at the end may be omitted. For example, each of the first resins 60A to 60C will be referred to as a first resin 60.

The first resin 60 is a flexible resin smaller in hardness than a second resin 70. The expression "smaller in hardness" indicates that "the Young's modulus is smaller". For example, the first resin 60 made of a silicone resin has a Young's modulus of 0.1 GPa, and the second resin 70 made of an ultraviolet curable epoxy resin has a Young's modulus of 2.0 GPa. The Young's moduli (elastic moduli) are measured at 25° C. in conformity to ASTM-D638.

Although not shown, the optical unit 5 also includes other optical elements such as a flare diaphragm and a brightness diaphragm. Any of the optical devices may be a spacer device having, at the center, a through-hole which serves as an optical path. In other words, a configuration such as the numbers of optical devices, spacers, and diaphragms of the optical unit according to an embodiment is set according to specifications.

The image pickup unit 50 includes an image pickup device 51 and a cover glass 52. The image pickup device 51 has alight receiving portion 51A configured to receive an object image focused by the optical unit 5.

As will be described later, the optical devices 20 to 40 are molded products. For example, the optical device 20 is a polycarbonate resin formed by molding the spacers 25 on the third principal surface 20SA, and molding a convex lens on the fourth principal surface 20SB.

In the image pickup apparatus 1, it is not easy to adhere the plurality of optical devices 10 to 40 because the cross section of the optical device 10 in the direction orthogonal to the optical axis O is as extremely slim as less than or equal to 1 mm square, for example, for making the endoscope 9 minimally invasive.

As will be described later, in the image pickup apparatus 1, the second resin 70 which is a curable resin shrinks by curing to apply a tensile stress (a force that pulls each of the principal surfaces) to the fourth principal surface 20SB and the fifth principal surface 30SA. This reduces the interval between the fourth principal surface 20SB and the fifth principal surface 30SA, and the fourth principal surface 20SB is brought into contact with the spacers 35. Until the fourth principal surface 20SB is brought into contact with the spacers 35, the tensile stress decreases as the second resin 70 shrinks by curing.

In the image pickup apparatus 1, a residual stress (hereinafter referred to as a "shrinking force") of the second resin after curing is smaller than in an image pickup apparatus having a conventional configuration in which the fourth principal surface is in contact with the spacers before the second resin starts shrinking by curing, and the interval between the fourth principal surface and the fifth principal surface is not reduced by shrinking by curing.

Note that in the present invention, the first resin 60 having the same thickness as the uncured second resin 70 is flexible, and thus, when the second resin 70 shrinks by curing, the first resin 60 shrinks with the shrinkage of the second resin 70. Therefore, the first resin 60 applies a compression stress (a force that presses each of the principal surfaces) to the fourth principal surface 20SB and the fifth principal surface 30SA. The compression stress of the first resin 60 is smaller than the tensile stress of the fourth resin.

The endoscope 9 including the image pickup apparatus 1 is minimally invasive because of the small diameter, and is easy to manufacture and highly reliable because of the low likelihood of detachment of gluing interfaces among the optical devices 10 to 40.

<Manufacturing Method of Image Pickup Apparatus for Endoscope>

Figure 6:
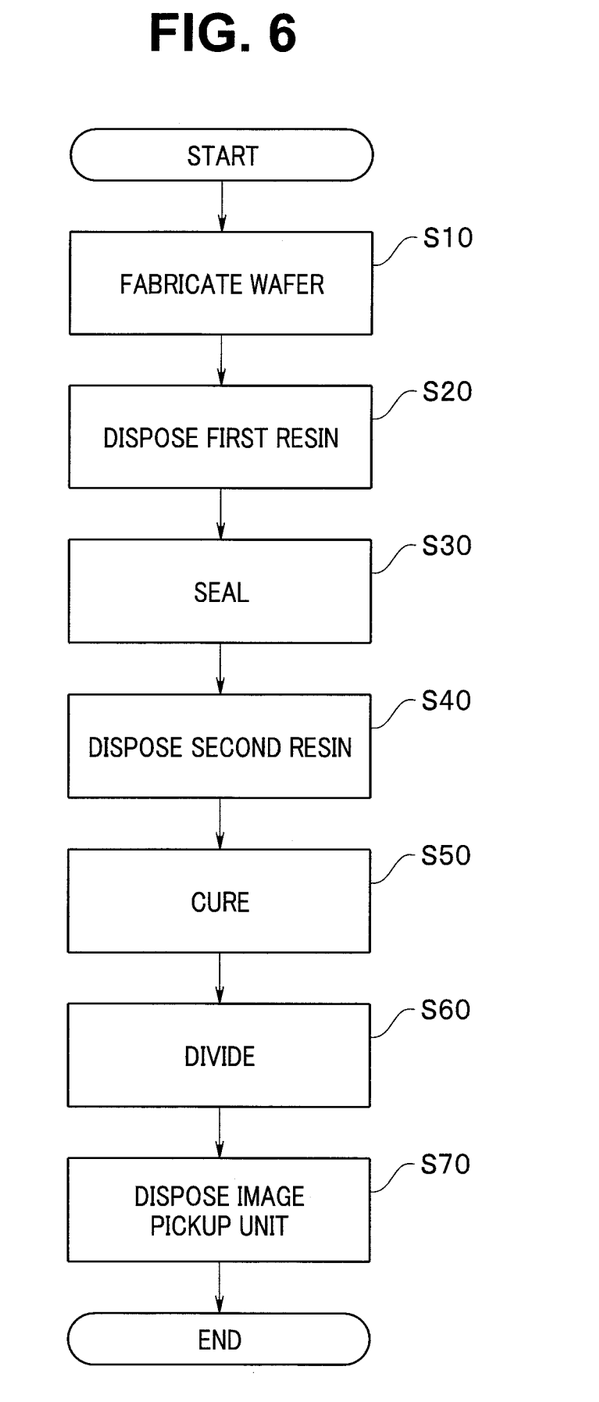
FIG. 6 is a flowchart of a manufacturing method of the image pickup apparatus according to an embodiment.

A manufacturing method of the image pickup apparatus for endoscope according to the present embodiment will be described in line with the flowchart shown in FIG. 6. Note that the first optical device 10 and the second optical device 20 will be described below. For example, a gluing method of the second optical device 20 and the third optical device 30, and a gluing method of the third optical device 30 and the fourth optical device 40 are generally the same as a gluing method of the first optical device 10 and the second optical device 20.

<Step S10> Wafer Fabricating Step

Figure 7:
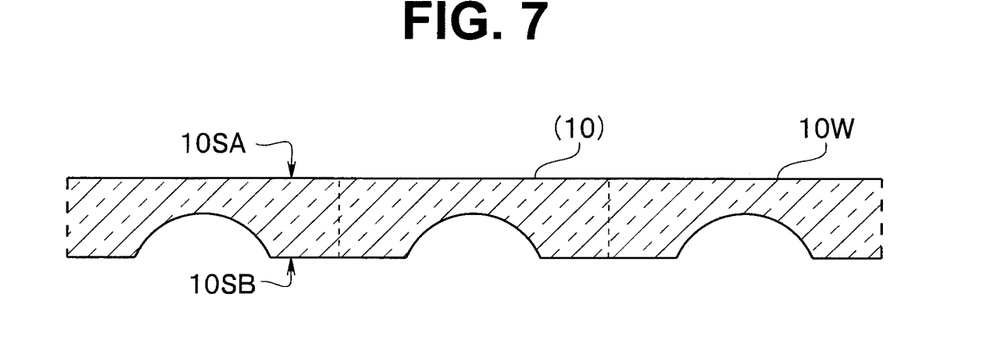
FIG. 7 is a sectional view for describing the manufacturing method of the image pickup apparatus according to an embodiment.
Figure 8:
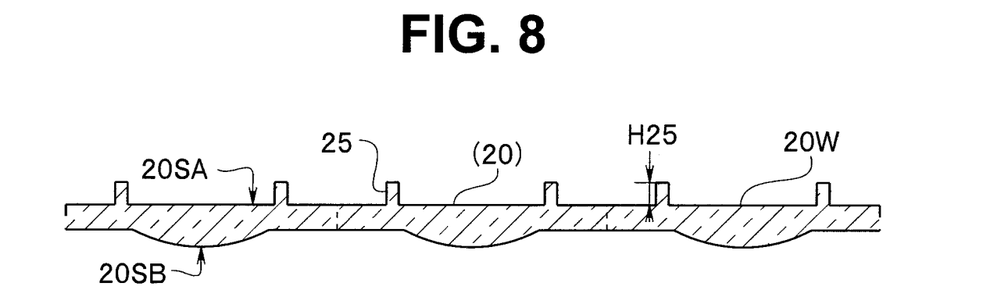
FIG. 8 is a sectional view for describing the manufacturing method of the image pickup apparatus according to an embodiment.

As shown in FIG. 7, a first optical wafer 10W having the first principal surface 10SA and the second principal surface 10SB on the opposite side of the first principal surface 10SA, and including a plurality of first optical devices 10 is fabricated. As shown in FIG. 8, a second optical wafer 20W having the third principal surface 20SA and the fourth principal surface 20SB on the opposite side of the third principal surface 20SA, and including a plurality of second optical devices 20 respectively including the spacers 25 on the third principal surface 20SA is fabricated.

The optical wafers 10W and 20W are made of a transparent rigid resin. For example, by molding an optical resin by an injection molding method or a press molding method, the optical wafers 10W and 20W including the plurality of optical devices 10 and 20 having a predetermined shape are fabricated. Examples of the transparent rigid resin include polycarbonate having a Young's modulus of 5 GPa.

The plurality of spacers 25 which are columns having the height H25 are molded on the third principal surface 20SA of the optical wafer 20W. The plurality of spacers 25 are arranged to enclose the optical path. The height H25 of the spacers 25 fabricated by molding is managed accurately to have a predetermined value because the shape of a mold is transferred.

The optical wafers 10W and 20W may be a hybrid lens wafer formed by disposing lenses and spacers made of a resin on parallel flat glass wafers.

A configuration of the optical wafers, that is, materials, shapes, numbers, arrangements, and outer shapes, and the like of the optical devices as arranged are designed according to specifications.

<Step S20> First Resin Disposing Step

Figure 9:
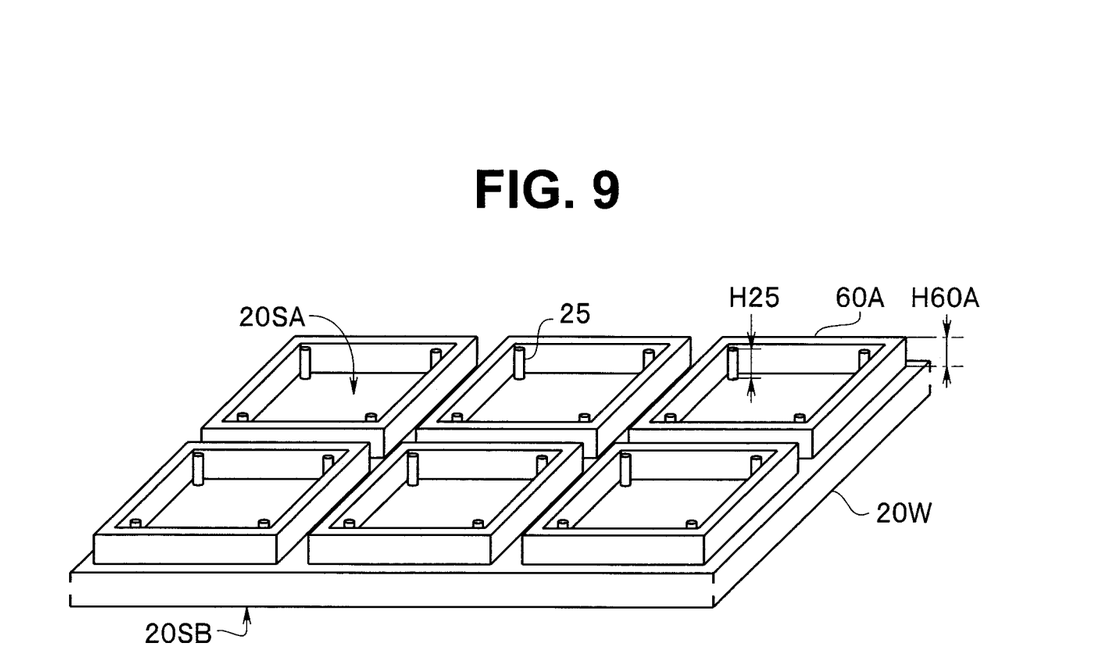
FIG. 9 is a perspective view for describing the manufacturing method of the image pickup apparatus according to an embodiment.

As shown in FIG. 9, a plurality of frame-like walls 60A made of the first resin and enclosing respective optical paths without any gap are disposed on the third principal surface 20SA of the second optical wafer 20W. The height H60A of the walls 60A is greater than the height H25 of the spacers 25.

Note that the walls 60A may be disposed on the second principal surface 10SB of the first optical wafer 10W.

The walls 60A may be disposed by a screen printing method or an ink jet method, but preferably is disposed using a film made of the first resin. For example, the plurality of walls 60A made of the first resin held on a holding film and patterned into a predetermined shape are transferred to the optical wafer 10W or the optical wafer 20W.

<Step S30> Sealing Step

Figure 10:
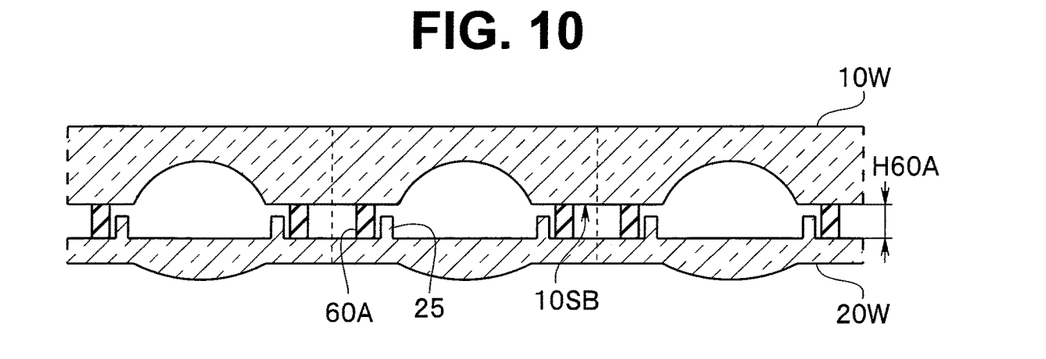
FIG. 10 is a sectional view for describing the manufacturing method of the image pickup apparatus according to an embodiment.

As shown in FIG. 10, the optical paths are sealed by clamping the second principal surface 10SB of the first optical wafer 10W and the third principal surface 20SA of the second optical wafer 20W with the plurality of walls 60A being interposed between the second principal surface 10SB and the third principal surface 20SA. For example, when clamped at 80° C., the first optical wafer 10W and the second optical wafer 20W are adhered. Note that in a case where the first resin has viscosity, the first optical wafer 10W and the second optical wafer 20W are temporarily fixed merely by being clamped at a room temperature.

Note that since the first resin is flexible, the upper surface of the spacers 25 on the second optical wafer 20W and the second principal surface 10SB may be temporarily brought into contact when clamped. However, when left behind after the clamping, the first resin returns to the height H60A when being disposed because of a compression stress that causes the first resin to return to an original height. Therefore, a gap is produced between the spacers 25 and the second principal surface 10SB.

For example, in a case where the height H60A of the walls 60A is 50 μm, and the height H25 of the spacers 25 is 48 μm, a gap of 2 μm is produced between the spacers 25 and the second principal surface 10SB.

<Step S40> Second Resin Disposing Step

Figure 11:
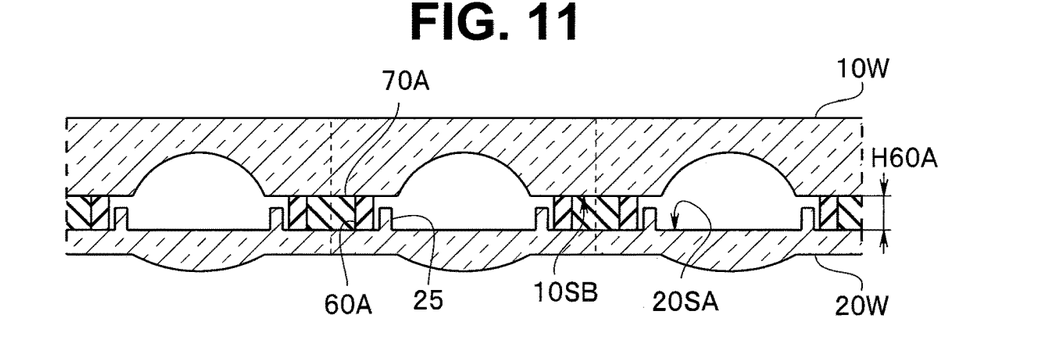
FIG. 11 is a sectional view for describing the manufacturing method of the image pickup apparatus according to an embodiment.

The uncured second resin 70A is charged between the second principal surface 10SB and the third principal surface 20SA around the walls 60A. The uncured second resin 70A is in liquid form, but the second resin 70A does not enter the optical paths since the optical paths are enclosed by the walls 60A made of the first resin. To dispose the liquid second resin 70A between the second principal surface 10SB and the third principal surface 20SA, it is preferable to utilize a capillary action.

<Step S50> Second Resin Curing Step

Figure 12:
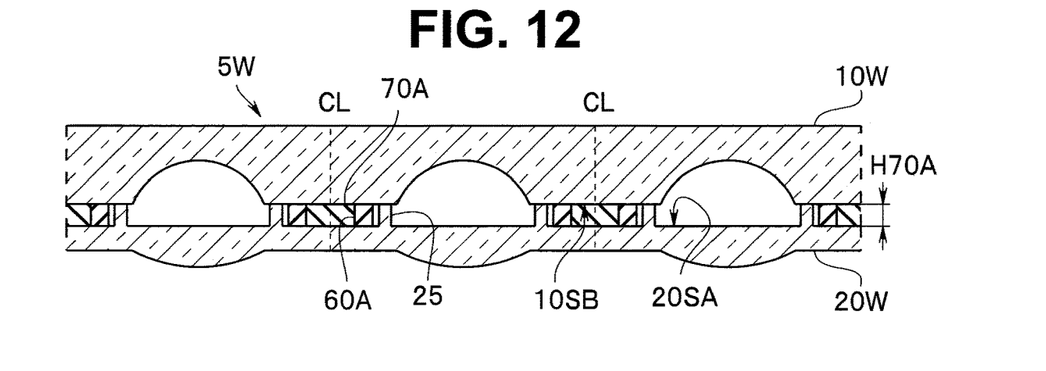
FIG. 12 is a sectional view for describing the manufacturing method of the image pickup apparatus according to an embodiment.

By performing curing treatment on the second resin 70A, the second resin 70A shrinks, and the interval between the second principal surface 10SB and the third principal surface 20SA decreases to be fixed in a state of the interval defined by the spacers 25.

In a case where the second resin 70A is an ultraviolet curable resin, the second resin 70A is irradiated with ultraviolet rays, and in a case where the second resin 70A is a thermally curable resin, heating treatment is performed. The liquid second resin 70A is solidified when cured, and adheres the first optical wafer 10W and the second optical wafer 20W.

In other words, the first resin constituting the walls 60A is a flexible resin smaller in hardness than the second resin 70A. Therefore, when the second resin 70A shrinks by the curing treatment, the walls 60A are compressed and deformed by the tensile stress of the second resin 70A. Thus, the second principal surface 10SB and the spacers 25 are brought into contact with each other.

As already described, in the case where the height H60A of the walls 60A is 50 μm, and the height H25 of the spacers 25 is 48 μm, there is a gap of 2 μm between the spacers 25 and the second principal surface 10SB. The second resin 70A charged between the second principal surface 10SB and the third principal surface 20SA has a thickness of 50 μm.

The height H60A of the walls 60A is set on the basis of a curing shrinkage ratio of the second resin 70A and the height H25 of the spacers 25. In a case where an amount of shrinkage of the second resin 70A caused by a curing reaction is more than or equal to 1% and less than or equal to 10%, for example, the height H60A of the walls 60A disposed in the first resin disposing step S20 is more than or equal to 101% and less than or equal to 110% of the height H25 of the spacers 25.

Preferably, the first resin is a flexible resin having a Young's modulus of less than or equal to 1 GPa, and the second resin 70A after curing is a rigid resin having a Young's modulus of more than 1 GPa More preferably, the first resin has a Young's modulus of less than or equal to 0.5 GPa, and the second resin 70A has a Young's modulus of more than or equal to 2 GPa.

Note that the spacers 25 are more rigid than the second resin 70A. The spacers 25 are made of a rigid resin having a Young's modulus of more than 2 GPa, for example.

The first resin is selected from among a flexible silicone resin, rubber, and the like. The second resin 70A and the spacers 25 (the second optical device 20) are selected from among epoxy resin, polystyrene resin, melanin resin, polycarbonate resin, and the like.

As long as the Young's moduli of the resins fall within the above ranges, the walls 60A made of the first resin are deformed by compression when the second resin 70A shrinks, and the optical path length is defined by the spacers 25.

Shrinkage of the second resin 70A having been cured is restricted by the spacers 25. Therefore, the second resin 70A applies a tensile stress to the second principal surface 10SB and the third principal surface 20SA. The tensile stress is a force that acts in a direction in which the second principal surface 10SB and the third principal surface 20SA are brought closer to each other. On the other hand, the first resin being compressed applies a compression stress to the second principal surface 10SB and the third principal surface 20SA. The compression stress is a force that acts in a direction in which the second principal surface 10SB and the third principal surface 20SA are pulled away from each other.

The shrinking force of the second resin 70A (a tensile stress remaining in the second resin 70A) is smaller than in a case where the first resin is not required. Therefore, a great shrinking force does not act on the gluing interfaces of the optical unit 5, so that gluing reliability is high.

Note that the tensile stress of the second resin 70A is designed to be greater than the compression stress of the first resin. Therefore, when the second resin 70A shrinks by curing, the interval between the second principal surface 10SB and the third principal surface 20SA decreases.

<Step S60> Dividing Step

Figure 13:
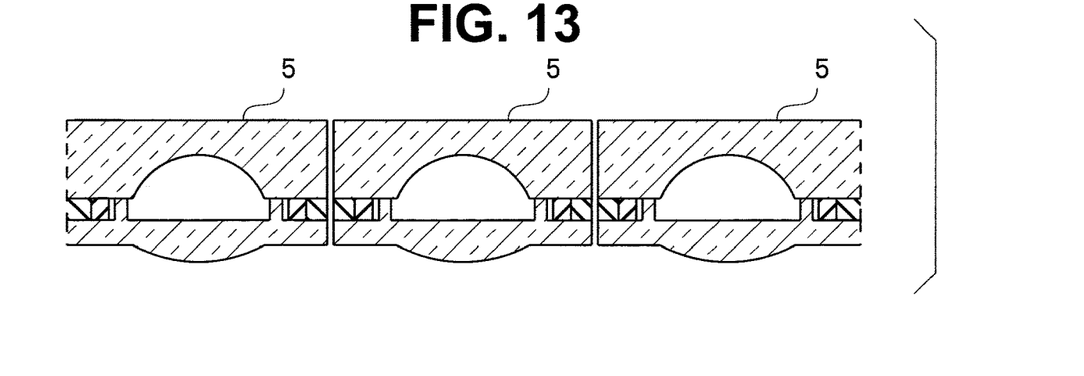
FIG. 13 is a sectional view for describing the manufacturing method of the image pickup apparatus according to an embodiment.

A bonded wafer 5W in which the first optical wafer 10W and the second optical wafer 20W are fixed by the second resin 70A is divided to fabricate the optical unit 5.

As shown in FIG. 13, the bonded wafer is cut along cutting lines CL with a dicing blade to be divided into a plurality of optical units 5. Laser dicing or plasma dicing may be used for the cutting.

Note that although the optical units 5 have a rectangular parallelepiped shape, the bonded wafer may be divided into hexagonal columnar image pickup apparatuses, for example, depending on an arrangement of the cutting lines CL in the bonded wafer. Alternatively, the shape of the optical units 5 may be made columnar by processing after the division. In other words, the shape of the optical units 5 is not limited to a rectangular parallelepiped shape.

<Step S70> Image Pickup Unit Disposing Step

The image pickup unit 50 configured to receive an object image focused by the optical unit 5 is disposed on the optical unit 5. The image pickup unit 50 is fabricated by forming the light receiving portion 51A in an image pickup device wafer composed of a silicon wafer by a publicly-known semiconductor manufacturing technology, gluing a glass wafer for protecting the light receiving portion 51A, and then cutting the wafers.

Note that the image pickup unit 50 on which the optical unit 5 is disposed may be fabricated by gluing the image pickup device wafer, for example, to the bonded wafer including the plurality of optical units 5 and then cutting the wafers. Alternatively, a plurality of image pickup units 50 may be adhered to the bonded wafer including the plurality of optical units 5, and then cutting may be performed. In other words, the dividing step S60 and the image pickup unit disposing step S70 may be reversed in order, or may be performed simultaneously.

The curing shrinkage ratio of the second resin 70A varies according to curing conditions, chronological changes after curing, and the like. However, in the optical unit 5, the interval between the second principal surface 10SB and the third principal surface 20SA is defined by the height H25 of the spacers 25. The image pickup apparatus 1 has a favorable optical property since the optical path length of the optical unit 5 is stable.

Since the shrinking force of the second resin 70A produced by curing (the tensile stress remaining in the second resin 70A) is smaller than in a case where the first resin 60 is not required, the gluing interfaces have high gluing reliability. Therefore, the image pickup apparatus 1 and the endoscope 9 including the image pickup apparatus 1 have high reliability.

Note that the image pickup apparatus 1 includes the optical unit 5 formed by stacking the four optical devices 10 to 40. However, it is apparent that as long as at least two optical devices are stacked in a manner similar to the optical unit 5, the same effects as effects of the image pickup apparatus 1 are exerted.

In other words, the image pickup apparatus for endoscope according to the present invention includes an optical unit, and an image pickup unit configured to receive an object image focused by the optical unit. The optical unit includes: a first optical member including a first principal surface and a second principal surface on an opposite side of the first principal surface; a second optical member including a third principal surface and a fourth principal surface on an opposite side of the third principal surface, the third principal surface being opposed to the second principal surface, the second optical member including a spacer on the third principal surface around an optical path, the spacer defining an interval between the second principal surface and the third principal surface; a first resin constituting a wall that seals the optical path between the second principal surface and the third principal surface, is equal in height to the spacer, and encloses the optical path without any gap; and a second resin charged around the wall and being equal in height to the spacer. The first resin is smaller in hardness than the second resin.

The manufacturing method of an image pickup apparatus for endoscope according to the present invention includes: a wafer fabricating step of fabricating a first optical wafer including a first principal surface and a second principal surface on an opposite side of the first principal surface, and including a plurality of first optical devices, and a second optical wafer including a third principal surface and a fourth principal surface on an opposite side of the third principal surface, and including a plurality of second optical devices respectively including spacers on the third principal surface; a first resin disposing step of disposing a plurality of walls on the second principal surface or the third principal surface, the plurality of walls being made of a first resin, being greater in height than the spacers, and enclosing respective optical paths without any gap; a sealing step of sealing the optical paths by clamping the second principal surface and the third principal surface with the walls being interposed between the second principal surface and the third principal surface; a second resin disposing step of charging a second resin between the second principal surface and the third principal surface around the walls, the second resin being uncured and liquid; a curing step of performing curing treatment on the second resin to cause the second resin to shrink, and fix the second principal surface and the third principal surface in a state where an interval between the second principal surface and the third principal surface is defined by the spacers; and a dividing step of cutting a bonded wafer in which the first optical wafer and the second optical wafer are fixed by the second resin.

<Modifications>

Image pickup apparatuses 1A to 1D and manufacturing methods of the image pickup apparatuses 1A to 1D according to modifications are respectively similar to the image pickup apparatus 1 and the manufacturing method of the image pickup apparatus 1, and exert the same effects. Thus, components having the same function will be denoted by the same reference numeral, and description will be omitted.

<Modification 1>

Figure 14:
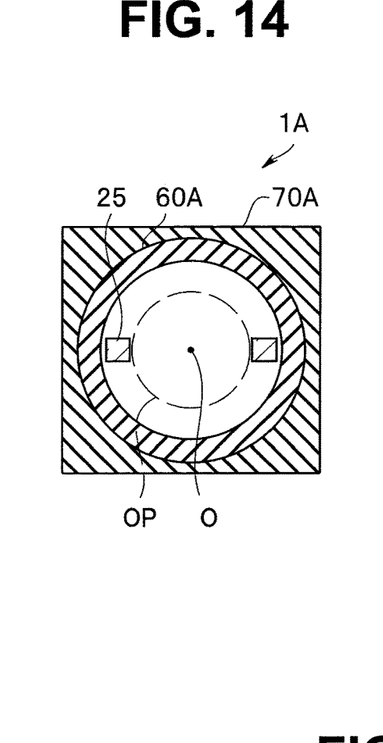
FIG. 14 is a sectional view of an optical unit of an image pickup apparatus according to Modification 1.

As shown in FIG. 14, in the image pickup apparatus 1A according to Modification 1, two prismatic spacers 25 are arranged at rotationally symmetric positions about the optical axis O. The wall 60A made of the first resin that encloses the optical path OP is ring-shaped.

<Modification 2>

Figure 15:
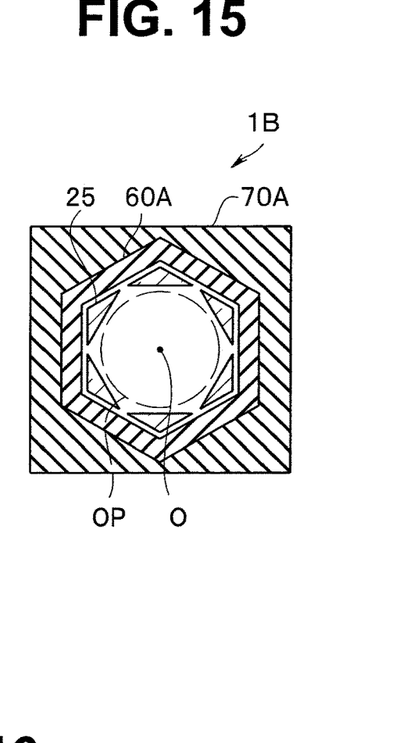
FIG. 15 is a sectional view of an optical unit of an image pickup apparatus according to Modification 2.

As shown in FIG. 15, in the image pickup apparatus 1B according to Modification 2, six triangular prismatic spacers 25 are arranged at rotationally symmetric positions about the optical axis O. The wall 60A made of the first resin that encloses the optical path OP is hexagonal.

In other words, the shape and number of the spacers 25 can be selected as appropriate as long as the spacers 25 can define an interval, that is, an optical path length. As long as the wall 60A made of the first resin encloses the optical path OP without any gap, the shape of the wall 60A can be selected as appropriate.

<Modification 3>

Figure 16:
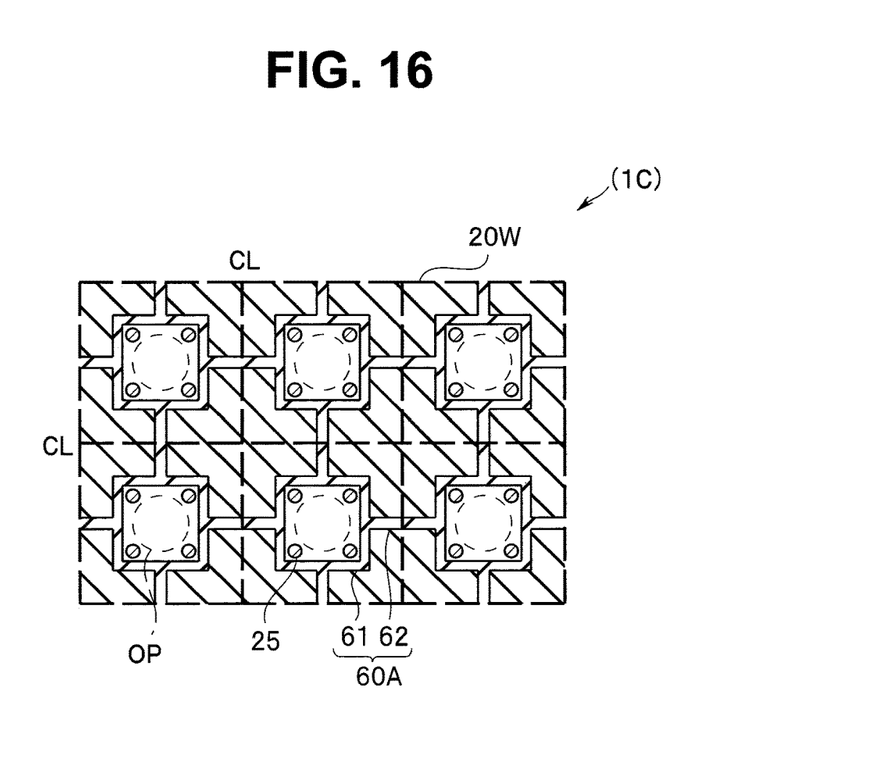
FIG. 16 is a sectional view for describing a manufacturing method of an image pickup apparatus according to Modification 3.

As shown in FIG. 16, the plurality of walls 60A made of the first resin and disposed on the second optical wafer 20W for fabricating the image pickup apparatus 1C according to Modification 3 are connected to each other.

The walls 60A include main portions 61 each enclosing the optical path OP and connecting portions 62 that connect the plurality of main portions 61. A height H61 of the main portions 61 is greater than the height H25 of the spacers 25. A height H62 of the connecting portions 62 is smaller than the height H25 of the spacers 25. Even when the optical paths OP are sealed by the main portions 61, there is a gap between the connecting portions 62 and the second principal surface 10SB of the first optical wafer 10W. Therefore, the second resin 70A can be charged into the gap.

In the image pickup apparatus 1C, the plurality of walls 60A are easy to be disposed on the second optical wafer 20W since the plurality of walls 60A are connected to each other.

<Modification 4>

Figure 17:
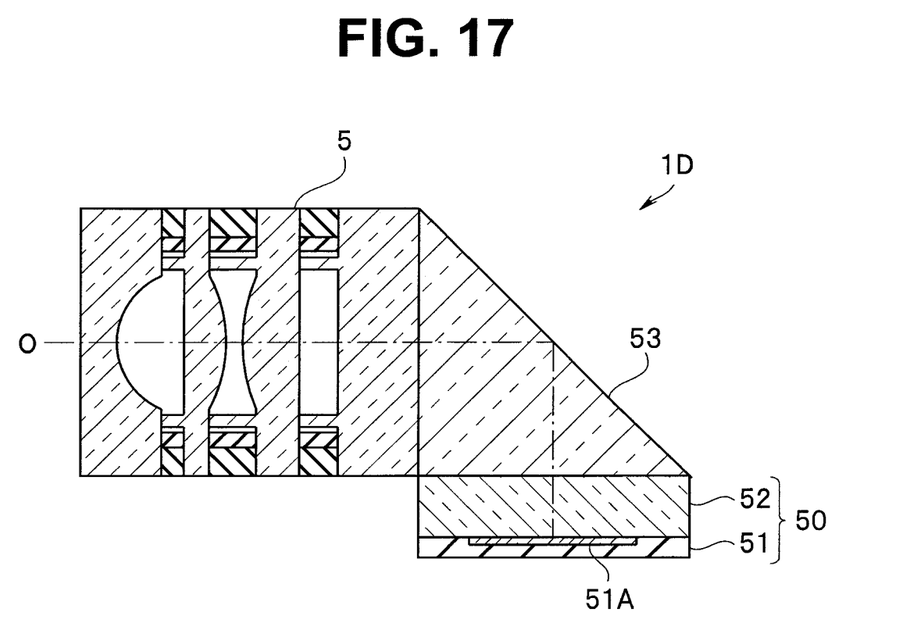
FIG. 17 is a sectional view of an image pickup apparatus according to Modification 4.

As shown in FIG. 17, the image pickup apparatus 1D according to Modification 4 is what is called a horizontally-placed type in which the light receiving portion 51A of the image pickup device 51 is arranged parallel to the optical axis O of the optical unit 5.

An object image focused by the optical unit 5 is reflected by a prism 53, and enters the light receiving portion 51A of the image pickup device 51.

Note that needless to say, endoscopes 9A to 9D respectively including the image pickup apparatuses 1A to 1D have effects of the endoscope 9 including the image pickup apparatus 1, and furthermore, have effects of the respective image pickup apparatuses 1A to 1D.

The present invention is not limited to the above-described embodiments and the like, and various changes, alterations, and the like can be made within a range in which the gist of the present invention is not changed.

What is claimed is:

1. A manufacturing method of an image pickup apparatus for use with an endoscope, the method comprising:
    fabricating a first optical wafer including a first surface and a second surface on an opposite side of the first surface, and a second optical wafer including a third surface and a fourth surface on an opposite side of the third surface, and a plurality of spacers on the third surface;
    disposing a wall between the second surface and the third surface to surround the plurality of spacers, the wall made of a first resin, the wall being greater in height than the plurality of spacers;
    subsequent to the disposing of the wall, clamping the first optical wafer and the second optical wafer together with the wall being interposed between the second surface and the third surface to seal an outer periphery of the wall to each of the second surface and the third surface;
    filling a second resin between the second surface and the third surface around the outer periphery of the wall, the second resin being uncured and liquid;
    curing the second resin to fix the second surface relative to the third surface; and
    cutting a bonded wafer in which the first optical wafer and the second optical wafer are fixed by the second resin.

2. The manufacturing method according to claim 1, wherein a height of the wall when the wall made of the first resin is disposed is more than or equal to 101% and less than or equal to 110% of a height of the plurality of spacers.

3. The manufacturing method according to claim 2, wherein the wall is fabricated using a film made of the first resin.

4. The manufacturing method according to claim 3, wherein the first optical wafer and the second optical wafer are fabricated by molding.

5. An image pickup apparatus for use with an endoscope, the image pickup apparatus comprising:
    an optical unit; and
    an image pickup unit configured to receive an object image focused by the optical unit,
    wherein the optical unit includes:
        a first optical member including:
            a first surface; and
            a second surface on an opposite side of the first surface;
        a second optical member including:
            a third surface; and
            a fourth surface on an opposite side of the third surface, and
        a spacer on the third surface, the spacer defining an interval between the second surface and the third surface;
        a wall made of a first resin, the wall sealing a space between the second surface and the third surface, the wall is equal in height to the spacer; and
        a second resin filled around an outer periphery of the wall, the second resin being equal in height to the spacer, and
    wherein the first resin is smaller in hardness than the second resin.

6. The image pickup apparatus according to claim 5, wherein the second resin is a curable resin.

7. The image pickup apparatus according to claim 6, wherein a tensile stress of the second resin is greater than a compression stress of the first resin.

8. The image pickup apparatus according to claim 5, wherein both the first optical member and the second optical member are molded products.

9. An endoscope comprising:
    an image pickup apparatus comprising:
        an optical unit; and
        an image pickup unit configured to receive an object image focused by the optical unit,
    wherein the optical unit includes:
        a first optical member including:
            a first surface; and
            a second surface on an opposite side of the first surface;
        a second optical member including:
            a third surface; and
            a fourth surface on an opposite side of the third surface, and
        a spacer on the third surface, the spacer defining an interval between the second surface and the third surface;
        a wall made of a first resin, the wall sealing a space between the second surface and the third surface, the wall is equal in height to the spacer; and
        a second resin filled around an outer periphery of the wall, the second resin being equal in height to the spacer, and
    wherein the first resin is smaller in hardness than the second resin.

10. The manufacturing method according to claim 1, further comprising releasing the clamping after the curing.

11. The manufacturing method according to claim 1, wherein the fixing is in a state where an interval between the second surface and the third surface is defined by the plurality of spacers.

12. The manufacturing method according to claim 1, wherein the plurality of spacers are integrally formed with the second optical wafer as a single unitary piece.

13. The manufacturing method according to claim 1, wherein the clamping reduces a distance between the first and second optical wafers.

14. The manufacturing method according to claim 1, wherein the filling fills the second resin between the second surface and the third surface around the outer periphery of the wall from a space formed between the second surface and the third surface.

15. The manufacturing method according to claim 1, wherein the wall and the spacer extend from the third surface from difference positions on the third surface and at different heights from the third surface.

16. The image pickup apparatus according claim 5, wherein the spacer comprises at least first and second spacers located diagonally relative to each other on the second optical member with an optical axis positioned between the first spacer and the second spacer.

17. The image pickup apparatus according claim 5, wherein the spacer is integrally formed with the second optical wafer as a single unitary piece.

18. The endoscope according claim 9, wherein the spacer comprises at least first and second spacers located diagonally relative to each other on the second optical member with an optical axis positioned between the first spacer and the second spacer.

19. The endoscope according claim 9, wherein the wall encloses an optical path without any gap.

20. The endoscope according claim 9, wherein the spacer is integrally formed with the second optical wafer as a single unitary piece.

* * * * *